US005498613A

United States Patent [19]

Rodgers et al.

[11] Patent Number: 5,498,613
[45] Date of Patent: Mar. 12, 1996

[54] DIPYRIDAMOLE AND ANALOGS THEREOF IN PREVENTING ADHESION FORMATION

[75] Inventors: Kathleen E. Rodgers, Long Beach; Gere S. Dizerega, Pasadena, both of Calif.

[73] Assignee: The University of Southern California, Los Angeles, Calif.

[21] Appl. No.: 253,437

[22] Filed: Jun. 7, 1994

[51] Int. Cl.$^6$ .................................................. A61K 31/505
[52] U.S. Cl. ........................ 514/258; 424/450; 424/489; 424/490; 514/921; 606/151
[58] Field of Search ................................ 424/450, 489, 424/490; 514/921, 258; 606/151

[56] References Cited

U.S. PATENT DOCUMENTS

| | | | |
|---|---|---|---|
| 4,346,108 | 8/1982 | Singer | 424/317 |
| 4,538,596 | 9/1985 | Colasante | 128/32 |
| 4,889,722 | 12/1989 | Sheffield et al. | 424/450 |
| 4,911,926 | 3/1990 | Henry et al. | 424/426 |
| 4,937,254 | 6/1990 | Sheffield et al. | 514/576 |
| 5,002,551 | 3/1991 | Linsky et al. | 606/151 |
| 5,246,715 | 9/1993 | Orevi et al. | 424/450 |
| 5,364,622 | 11/1994 | Franz et al. | 514/57 |

OTHER PUBLICATIONS

Aznar–Salatti, J. et al., "Dipyridamole induces changes in the thrombogenic properties of extracellular matrix generated by endothelial cells in culture," *Thrombosis Research* 64, 341–353 (1991).

Brereton et al., "Effect of prostaglandin E1 alone and in combination with theophylline or aspirin on collagen–induced platelet aggregation and on platelet nucleotides including adenosine 3':5'-cyclic monophosphate," *Biochem. J.* 120, 709–718 (1970).

Bamford, C. H. et al., "Polymeric inhibitors of platelet aggregation. II. Copolymers of dipyridamole and related drugs with N-vinylpyrrolidone," *Biochim. Biophys. Acta* 924, 38–44 (1987).

Bjornsson, T. D. et al., "Effective antiplatelet drug concentrations in experimental arterial thromboembolism," *Thrombosis Research* 48, 337–348 (1987).

Boeynaems, J. M. et al., "Dipyridamole and vascular prostacyclin production," *Biochemical Pharmacol.* 35, 2897–2902 (1986).

Brozna, J. P. et al., "Dipyridamole inhibits $O_2$ release and expression of tissue factor activity by peripheral blood monocytes stimulated with lipopolysaccharide," *Thrombosis Research* 60, 141–156 (1990).

Bult, H. et al., "Dipyridamole potentiates platelet inhibition by nitric oxide," *Thrombosis & Haemostasis* 66, 343–349 (1991).

Chan, T. C. K. et al. "Pharmacokinetics of intraperitoneally administered dipyridamole in cancer patients," *Cancer Research* 48, 215–218 (1988).

Chatelut, E. et al., "A slow–release methotrexate formulation for intrathecal chemotherapy," *Cancer Chemother. Pharmacol.* 32, 179–182 (1993).

Colli, S. & Tremoli, E., "Multiple effects of dipyridamole on neutrophils and mononuclear leukocytes: adenosine–dependent and adenosine–independent mechanisms," *J. Lab. Clin. Med.* 118, 136–145 (1991).

Constantini, V. et al., "Increased prostacyclin production from human veins by dipyridamole: an in vitro and ex vivo study," *Biomed. Biochim. Acta* 49, 263–271 (1990).

Czejka, M. J. et al., "Clinical pharmacokinetics of 5–fluorouracil," *Drug Res.* 43, (1993).

Dawicki, D. D. et al., "Role of adenosine uptake and metabolism by blood cells in the antiplatelet actions of dipyridamole, dilazep and nitrobenzylthioinosine," *Biochemical Pharmacol.* 34, 3965–3972 (1985).

diZerega, G. S. & Rodgers, K., "Fibroblasts and Tissue Repair Cells," in *The Peritoneum*, diZerega, G. S. & Rodgers, K. E., eds., Springer–Verlag, New York, pp. 122–127, 130–144 (1992).

diZerega, G. S. & Rodgers, K., "Peritoneal Closure," in *The Peritoneum*, diZerega, G. S. & Rodgers, K. E., eds., Springer–Verlag, New York, pp. 278–280 (1992).

diZerega, G. S. & Rodgers, K. E., "Prevention of Postoperative Adhesions," in *The Peritoneum*, diZerega, G. S. & Rodgers, K. E., eds., Springer–Verlag, New York, pp. 307–369 (1992).

Durante, W. et al., "Platelet inhibition by an L–arginine–derived substance released by IL–1 beta–treated vascular smooth muscle cells," *Am. J. Physiol.* 261, H2024–30 (1991).

Durante, W. et al., "Plasmin potentiates induction of nitric oxide synthesis by interleukin–1 beta in vascular smooth muscle cells," *Am. J. Physiol.* 264, H617–24 (1993).

Doody, K. J. et al., "Recombinant tissue plasminogen activator reduces adhesion formation in a rabbit uterine horn model," *Fertil. Steril.* 51, 509–512 (1989).

Elkins, T. E., "Can a Pro–Coagulant Substance Prevent Adhesions?" in *Treatment of Post–Surgical Adhesions*, diZerega, G. S. et al., eds., Wiley–Liss, New York, pp. 103–112 (1990).

Fregnan, G. B. & Berte, F., "Enhancement of specific biological activity of dipyridamole by complexation with β–cyclodextrin," *Pharmacology* 40, 96–102 (1990).

Golan, et al., "The effect of prostaglandins and aspirin—an inhibitor of prostaglandin synthesis—on adhesion formation in rats," *Human Reproduction* 6, pp. 251–254 (1991).

Hasday, J. D. et al., "Dipyridamole stimulates urokinase production and suppresses procoagulant activity of rabbit (List continued on next page.)

Primary Examiner—Ronald W. Griffin
Attorney, Agent, or Firm—Robbins, Berliner & Carson

[57] ABSTRACT

Compositions and methods for prevention of adhesion formation, whereby an effective amount of at least one compound selected from dipyridamole and analogs thereof is administered as active agent for a period of time sufficient to permit tissue repair. The active agent is preferably administered in conjunction with a delivery vehicle (e.g., microcapsules, microspheres, lipid-based systems, viscous instillates and absorbable mechanical barriers) useful for maintaining local concentrations of the compound at an effective level.

15 Claims, No Drawings

OTHER PUBLICATIONS alveolar macrophages: a possible mechanism of antithrombotic action," *Blood* 69, 660–667 (1987).

Herschlag, A. et al., "The effect of interleukin–1 on adhesion formation in the rat," *Am. J. Obstet. Gynecol.* 165, 771–4 (1991).

INTERCEED(TC7) Adhesion Barrier Study Group, "Prevention of postsurgical adhesions by INTERCEED(TC7), an absorbable adhesion barrier: a prospective, randomized multicenter clinical study," *Fertility and Sterility* 51, 933–938 (1989).

Kim, T. K. et al., "Extended–release formulation of morphine for subcutaneous administration," *Cancer Chemother. Pharmacol.* 33, 187–190 (1993).

LeVraux, V. et al., "Inhibition of human monocyte TNF production by adenosine receptor agonists," *Life Sciences* 52, 1917–1924 (1993).

Lichtner, R. B. et al., "The pyrimido–pyrimidine derivatives RA233 and RX–RA85 affect cell cycle distribution of two murine tumour cell lines," *Eur. J. Cancer Clin. Oncol.* 25, pp. 945–951 (1989).

McBride, W. H. et al., "Effect of Interleukin 1, inflammation, and surgery on the incidence of adhesion formation and death after abdominal irradiation in mice," *Cancer Research* 49, 169–173 (1989).

Mammen, E. F., "An overview of dipyridamole," *Thrombosis Research* Supplement XII, 1–3 (1990).

Stozek et al., "Bioverfugbarkeit von Dipyridamol in Form von Liposomen", *Pharmazie* 41 H.9, pp. 645–647 (1986).

Nitelius et al., "Pharmacokinetic interaction of acetylsalicylic acid and dipyridamole", *British Journal of Clinical Pharmacology*, vol. 19, Issue 3, pp. 379–383 (Mar. 1985).

Nishmura et al., "Ibuprofen in the Prevention of Experimentally Induced Postoperative Adhesions", *The American Journal of Medicine*, pp. 102–106 (Jul. 13, 1984).

Mills et al., "The Influence on Platelet Aggregation of Drugs That Affect the Accumulation of Adenosine 3':5'–Cyclic Monophosphate in Platelets", *Bioch.*, vol. 121, pp. 185–196 (1971).

Rodgers, "Nonsteroidal Anti–Inflammatory Drugs (NSAIDs) in the Treatment of Postsurgical Adhesion", Treatment of Post Surgical Adhesions, Published by Wiley–Liss, Inc., pp. 119–129 (1990).

Isonishi et al., "Phase I and Pharmacokinetic Trial of Intraperitoneal Etoposide in Combination With the Multidrug–Resistance–Modulating Agent Dipyridamole", *Journal of the National Cancer Institute*, vol. 83, Issue 9, pp. 621–626 (May 1, 1991).

Newell et al., "The Effect of the Nucleoside Transport Inhibitor Dipyridamole on the Incorporation of [3H] Thymidine in the Rat", *Biochemical Pharmacology*, vol. 35, Issue 21, pp. 3871–3877 (Nov. 1, 1986).

Rodgers et al., "Effects of Tolmetin Sodium Dihydrate on Normal and Postsurgical Peritoneal Cell Function", *International Journal Immunopharmac.*, vol. 10, No. 2, pp. 111–119 (1988).

Sakuma et al., "Dipyridamole Potentiates the Anti–Aggregating Effect of Endothelium–Derived Relaxing Factor", *Thrombosis Research* Supplement XII, pp. 87–90 (1990).

Saniabadi et al., "Effect of Dipyridamole Alone and in Combination With Aspirin on Whole Blood Platelet Aggregation, PGI Generation, and Red Cell Deformability Ex Vivo in Man", *Cardiovascular Research*, vol. 25, Issue 3, pp. 177–183 (Mar. 1991).

Soderback et al., "Effect of Dipyridamole–Like Compound (R–E 244) on Aggregation and Cyclic AMP Accumulation in Human Platelets", *Thrombosis Research*, vol. 64, No. pp. 355–362 (1991).

Stringer et al., "Disposition of Oral Dipyridamole in Patients Undergoing Thallium 201 Myocardial Imaging", *Pharmacotherapy*, vol. 12, No. 2, pp. 83–87 (1992).

Suzuki et al., "Inhibition of Active Oxygen Generation by Dipyridamole in Human Polymorphonuclear Leukocytes", *European Journal of Pharmacology*, Molecular Pharmacology Section, vol. 227, pp. 395–401 (1992).

Suzuki et al., "Dipyridamole Enhances an Anti–Proliferative Effect of Interferon in Various Types of Human Tumor Cells", *Int. J. Cancer*, vol. 51, pp. 627–633 (1992).

Tzanakakis et al., "Prevention of Human Pancreatic Cancer Cell–Induced Hepatic Metastasis in Nude Mice by Dipyridamole and Its Analog RA–233", *Cancer*, vol. 71, Issue 8, pp. 2466–2471 (Apr. 15, 1993).

Zacharski et al., "Effect of Mopidamol on Survival in Carcinoma of the Lung and Colon: Final Report of Veterans Administration Cooperative Study No. 188", *Journal of the National Cancer Institute*, vol. 80, Issue 2, pp. 90–97 (Mar. 16, 1988).

DIPYRIDAMOLE AND ANALOGS THEREOF IN PREVENTING ADHESION FORMATION

BACKGROUND OF THE INVENTION

The present invention relates to the medical arts. In particular, the present invention is directed to compositions and methods for use in preventing the formation of postoperative adhesions in mammals, and in particular human patients.

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation between organ surfaces is complex and not entirely understood. The first step is believed to involve excess fibrin deposition to form a scaffold. Organization of the fibrin scaffold by cellular elements, including fibroblasts and mesothelial cells, then follows. Notwithstanding a lack of understanding of all of the mechanisms underlying the formation of intraperitoneal adhesions, it is clear that substantially more is involved in the process than simple mechanisms of cell to cell adhesion; moreover, agents which are known to prevent the adhesion of one cell to another do not necessarily have utility in preventing the formation of intraperitoneal adhesions.

Various approaches for the prevention of adhesion formation have been actively explored [diZerega, G. S. & Rodgers, K. E., "Prevention of Postoperative Adhesions," in *The Peritoneum*, diZerega, G. S. & Rodgers, K. E., eds., Springer-Verlag, New York, pp. 307–369 (1992)]. In general, the treatments fall into three categories: prevention of fibrin deposition in the peritoneal exudate; reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also been proposed, results obtained to date suggest that the use of procoagulants in areas of substantial bleeding may actually promote adhesion formation [Elkins, T. E., "Can a Pro-Coagulant Substance Prevent Adhesions?" in *Treatment of Post-Surgical Adhesions*, diZerega, G. S. et al., eds., Wiley-Liss, New York, pp. 103–112 (1990)].

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded polytetrafluoroethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solutions of dextran 70 (molecular weight=70,000) have been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: corticosteroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal antiinflammatory drugs in postoperative adhesion formation show promise [Rodgers, K. E., "Nonsteroidal anti-inflammatory drugs (NSAIDs) in the treatment of Postsurgical adhesion," in *Treatment of Post-Surgical Adhesions*, diZerega, G. S. et al., eds., Wiley-Liss, New York, pp. 119–129 (1990)], clinical evaluations of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide this drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to prevent adhesion formation in a variety of different contexts.

It is an object of the present invention to provide compositions and methods for the minimization or prevention of post-surgical adhesion formation.

SUMMARY OF THE INVENTION

In accordance with one aspect of the present invention, there is provided a composition for the minimization or prevention of adhesion formation comprising at least one compound selected from the group consisting of dipyridamole and analogs thereof as active agent in a drug delivery system which maintains an effective concentration of the compound at a site of potential adhesion formation (e.g., a site of surgical trauma) during the perioperative interval. Pursuant to another aspect of the present invention, adhesion formation is minimized or prevented by administration of at least one active agent as defined herein at a site of potential adhesion formation for a period of time sufficient to permit substantial tissue repair (e.g., re-epithelialization, mesothelial repair) at the site.

DETAILED DESCRIPTION OF THE INVENTION

The inventive composition and method are useful in minimizing or preventing adhesion formation, the most common cause of which is prior surgery. The inventive composition and method have been shown to be especially effective in preventing the formation of adhesions between organ surfaces, in particular adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For example, prevention of adhesion formation or drug loculation during the intraperitoneal administration of chemotherapeutic agents is contemplated as within the scope of the present invention. For the purposes of the following discussion, attention is directed primarily to description of compositions and methods useful in inhibiting peritoneal adhesion formation.

The present invention contemplates the use of at least one compound selected from the group consisting of dipyridamole and analogs thereof. Presently preferred is dipyridamole; it has the formula 2,2',2",2"'-(4,8-dipiperidinopyrimido[5,4-d]pyrimidine-2,6-diyldinitrilo)tetraethanol or, using alternative nomenclature, 2,6-bis(diethanolamino)-4, 8-dipiperidinopyrimido-[5,4d]pyrimidine. Other suitable analogs include, but are not limited to, the following: RA 233 (mopidamol), with the chemical formula 2,6-bis(diethylamino)-4-piperidinopyrimido[5,4d] pyrimidine or 2,4,6-tri-morpholino-pyrimido (5,4-d)-pyrimidine [Mills, D. C. B. & Smith, J. B., "The influence on platelet aggregation of drugs that affect the accumulation of adenosine 3':5'-cyclic monophosphate in platelets," Biochem. J. 121, 185 (1971); Zacharski, L. R. et al., "Effect of mopidamol on survival in carcinoma of the lung and colon: final report of Veterans Administration Cooperative Study No. 188," J. Natl. Cancer Inst. 80, 90 (1988); Lichtner, R. B. et al., "The pyrimido-pyrimidine derivatives RA233 and RX-RA85 affect cell cycle distribution of two murine turnout cell lines," Eur. J. Cancer Clin. Oncol. 25, 945 (1989)]; R-E 244, with the structural formula 4 -(ethanolisopropanolamino)-2,7-di-(2'-methylmorpholino)-6-phenylpterine [Soederbaeck, U. & Sollevi, A., "Effect of dipyridamole-like compound (R-E 244) on aggregation and cyclic AMP accumulation in human platelets," Thromb. Res. 64, 355 (1991); Ball, G. et al., "Effect of prostaglandin E1 alone and in combination with theophylline or aspirin on collagen-induced platelet aggregation and on platelet nucleotides including adenosine 3':5'-cyclic monophosphate," Biochem. J. 120, 709 (1970)]; and RX-RA85, 4-(1-oxidothiomorpholino)-8 -phenethylthio-2-piperazino-pyrimido(5,4-d)pyrimidine [Lichtner et al., supra]. In addition to the neat forms, dipyridamole and analogs thereof may suitably be employed in the form of copolymers with, e.g., N-vinylpyrrolidone [Bamford, C. H. et al., "Polymeric inhibitors of platelet aggregation. II. Copolymers of dipyridamole and related drugs with N-vinylpyrrolidone," Biochim. Biophys. Acta 924, 38 (1987)]; hereinafter, reference to dipyridamole and analogs thereof is intended to refer to both the neat and the copolymer forms. Dipyridamole analogs suitable for use in accordance with the present invention are described in, e.g., Barnford, C. H. et al., "Influence of molecular structure on the synergistic action of theophylline or dipyridamole derivatives in the prostaglandin-type inhibition of platelet aggregation," J. Biomater. Sci. Polym. Ed. 2, 37 (1991), the entire disclosure of which is hereby incorporated by reference. The preparation of these known compounds has heretofore been disclosed in the literature; in addition, several of these compounds are available commercially.

Clinically, dipyridamole has been used primarily to reduce postoperative thromboembolism, particularly in patients with heart valve replacements and artificial heart valves [Mammen, E. F., "An overview of dipyridamole," Thrombosis Research Supplement XII, 1 (1990)]. It is believed that this occurs through inhibition of platelet aggregation mediated by adenosine [Boeynaems, J. M. et al., "Dipyridamole and vascular prostacyclin production," Biochemical Pharmacol. 35, 2897 (1986); Tzanakakis, G. N. et al., "Prevention of human pancreatic cancer cell-induced hepatic metastasis in nude mice by dipyridamole and its analog RA-233," Cancer 71, 2466 (1993)] and/or through an increase in $PGI_2$ production [Constantini, V. et al., "Increased prostacyclin production from human veins by dipyridamole: an in vitro and ex vivo study," Biomed. Biochim. Acta 49, 263 (1990)]. In addition, dipyridamole has been shown to have utility as a vasodilator, particularly in diagnostic assays [Stringer, K. A. et al., "Disposition of oral dipyridamole in patients undergoing thallium 201 myocardial imaging," Pharmacotherapy 12, 83 (1992)] and as an adjunct to other chemotherapeutic agents, making it possible to kill tumor cells at a lower concentration of antineoplastic drug [see, e.g., Czejka, M. J. et al., "Clinical pharmacokinetics of 5-fluorouracil," Drug Res. 43, 387 (1993); Isonishi, S., "Phase I and Pharmacokinetic Trial of Intraperitoneal Etoposide in Combination with the Multidrug-Resistance-Modulating Agent Dipyridamole," J. Nat'l Cancer Inst. 83, 621 (1991)].

Dipyridamole has also be suggested as having beneficial effects in disorders characterized by extravascular fibrin depositon (e.g., glomerulonephritis), decreasing the expression of tissue thromboplastin activity while concurrently stimulating the production and release of urokinase [Hasday, J. D. et al., "Dipyridamole stimulates urokinase production and suppresses procoagulant activity of rabbit alveolar macropbages: a possible mechanism of antithrombotic action," Blood 69, 660 (1987)]. Dipyridamole is therefore suggested to prevent fibrin accumulation at sites of inflammation through its direct effects on mononuclear phagocytes. It is further speculated that dipyridamole acts on the red cell membrane, rather than on platelets [Saniabadi, A. R. et al., "Effect of dipyridamole alone and in combination with aspirin on whole blood platelet aggregation, $PGI_2$ generation, and red cell deformability ex vivo in man," Cardiovascular Research 25, 177 (1991)]; dipyridamole increased red cell deformability and strongly inhibited red cell induced platelet activation. Dipyridamole has also been shown to modify the thrombogenic properties of the extracellular matrix produced by endothelial cell monolayers in culture [Aznar-Salatti, J. et al., "Dipyridamole induces changes in the thrombogenic properties of extracellular matrix generated by endothelial cells in culture," Thrombosis Research 64, 341 (1991)]; it is speculated that dipyridamole induces changes in endothelial metabolism which affect the composition of the extracellular matrix, rendering it less thrombogenic.

While the present invention is not bound to any particular theory, it is believed that the active agents of the present invention (and in particular, dipyridamole) may inhibit adhesion formation through a variety of mechanisms. Inhibition of platelet aggregation leads to a reduction in fibrin deposition; this contributes to a reduced rate of peritoneal adhesion formation. In addition, altered macrophage function and reduced procoagulant activity would reduce coagulation, and thus reduce fibrin deposition as well. The anti-inflammatory effects of dipyridamole lead to a reduction in secretion of tumor necrosis factor (a proinflammatory cytokine) by macrophages and in synthesis of leukotrienes by polymorphonuclear leukocytes (PMNs) [LeVraux, V. et al., "Inhibition of human monocyte TNF production by adenosine receptor agonists," *Life Sciences* 52, 1917 (1993)]. Dipyridamole leads to an increase in prostacyclin synthesis; prostacyclin has been shown to inhibit adhesion formation. Finally, dipyridamole has been shown to increase production of urokinase by macrophages; higher concentrations of urokinase lead to an acceleration of fibrin removal [Doody, K. J. et al., "Recombinant tissue plasminogen activator reduces adhesion formation in a rabbit uterine horn model," *Fertil. Steril.* 51, 509 (1989)].

As is well recognized in the art, however, no one of these possible mechanisms of action of dipyridamole would in and of itself be sufficient to enable one to predict whether these compounds would have any utility in reduction of adhesion formation.

For example, it is known that certain agents which inhibit platelet aggregation (for example, IL-1) actually promote adhesion formation [McBride, W. H. et al., "Effect of Interleukin 1, inflammation, and surgery on the incidence of adhesion formation and death after abdominal irradiation in mice," *Cancer Research* 49, 169–173 (1989); Herschlag, A. et al., "The effect of interleukin-1 on adhesion formation in the rat," *Am. J. Obstet. Gynecol.* 165, 771–4 (1991); Durante, W. et al., "Platelet inhibition by an L-arginine-derived substance released by IL-1 beta-treated vascular smooth muscle cells" *Am. J. Physiol.* 261, H2024–30 (1991)]. Nonetheless, IL-1 is believed to act through nitric oxide [Durante, W. et al., "Plasmin potentiates induction of nitric oxide synthesis by interleukin-1 beta in vascular smooth muscle cells," *Am. J. Physiol.* 264, H617-24 (1993); Schini, V. B. et al., "Thrombin inhibits induction of nitric oxide synthase in vascular smooth muscle cells," *Am. J. Physiol.* 264, H611-6 (1993)]. It has also been suggested that dipyridamole potentiates the inhibition of aggregation due to nitric oxide [Sakuma, I. et al., "Dipyridamole potentiates the anti-aggregating effect of endothelium-derived relaxing factor," *Thrombosis Research* Suppl. XII, 87 (1990)], perhaps by raising the sensitivity of the platelets for NO or prolonging the time and distance over which anti-platelet effects of NO are expressed [Bult, H. et al., "Dipyridamole potentiates platelet inhibition by nitric oxide," *Thrombosis & Haemostasis* 66, 343 (1991)].

Similarly, prostaglandins of the E series (PGE1 and PGE2) have been found to inhibit platelet aggregation [Ball et al., supra; Soederback & Sollevi, supra; Mills & Smith, supra]. Nonetheless, it has been shown that PGE2 increases adhesion formation [Golan, et al., "The effect of prostaglandins and aspirin—an inhibitor of prostaglandin synthesis—on adhesion formation in rats," *Human Reproduction* 6, 251 (1991)]. Therefore, there is clearly no correlation between inhibition of platelet aggregation and prevention in adhesion formation.

In addition, dipyridamole inhibits $O_2$ generation by neutrophils and mononuclear cells [Colli, S. & Tremoli, E., "Multiple effects of dipyridamole on neutrophils and mononuclear leukocytes: adenosine-dependent and adenosineindependent mechanisms," *J. Lab. Clin. Med.* 118, 136 (1991); Brozna, J. P. et al., "Dipyridamole inhibits $O_2^-$ release and expression of tissue factor activity by peripheral blood monocytes stimulated with lipopolysaccharide," *Thrombosis Research* 60, 141 (1990); Suzuki, S. et al., "Inhibition of active oxygen generation by dipyridamole in human polymorphonuclear leukocytes," *European J. Pharmacol.* 227, 395 (1992)]. In contrast, tolmetin (an agent also shown to reduce adhesion formation) has been shown to increase the production of oxygen radicals by postoperative macrophages [Rodgers, K. et al., "Effects of tolmetin sodium dihydrate on normal and postsurgical peritoneal cell function, *Int. J. Immunopharmac.* 10, 111 ( 1988)].

Further, dipyridamole has been reported to decrease procoagulant activity by macrophages [Colli & Tremoli, supra]. It has been suggested, however, that procoagulants may reduce adhesion formation [Elkins, supra].

Finally, dipyridamole has been reported to augment the cytotoxicity of several antimetabolites [Chan, T. C. K. et al. "Pharmacokinetics of intraperitoneally administered dipyridamole in cancer patients," *Cancer Research* 48, 215–218 (1988)] and enhance the anti-neoplastic properties of biological response modifiers [Suzuki, N. et al., "Dipyridamole enhances an anti-proliferative effect of interferon in various types of human tumor cells," *Int. J. Cancer* 51, 627 (1992)]. Cellular function (for example, proliferation of TRC to reepithelialize denuded surfaces) is required for adhesion prevention [diZerega, G. S. & Rodgers, K., "Fibroblasts and Tissue Repair Cells," in *The Peritoneum*, diZerega, G. S. & Rodgers, K. E., eds., Springer-Verlag, New York, pp. 1.22–144 (1992); diZerega, G. S. & Rodgers, K., "Peritoneal Closure," in *The Peritoneum*, diZerega, G. S. & Rodgers, K. E., eds., Springer-Verlag, New York, pp. 278–280 (1992)].

Pursuant to the method of the present invention, at least one active agent in accordance with the present invention is maintained in an effective concentration at the site of potential adhesion formation for a period of time sufficient to permit substantial re-epithelialization. The active agent is typically administered over the perioperative interval, which for purposes of the present invention may include time shortly prior to surgery through the surgery itself up to some time after completion of surgery. The term of administration may vary depending upon a number of factors which would be readily appreciated by those skilled in the art. In general, administration of a composition in accordance with the present invention including at least one active agent in accordance with the present invention should be effected from the time of surgery for at least 24 to 48 hours after completion of the surgical procedure. As healing is in most cases complete within about two weeks, it is generally not necessary to continue administration of a composition in accordance with the present invention much longer than two weeks. Preferably, a composition in accordance with the present invention comprising at least one active agent in accordance with the present invention is administered from about the time of surgery for a period of about 24 hours to about 7 days.

The rate of administration of the active agent in accordance with the present invention may be varied over a fairly broad range. The concentrations of active agent which can be administered would be limited by efficacy at the lower end and the solubility of the compound at the upper end. Uncomplexed dipyridamole has a poor bioavailability and has heretofore been characterized by a narrow therapeutic index in man: at blood levels above about 2–2.5 µg/ml, the compound might give side effects (mainly headache and nausea; below about 0.5 µg/ml, useful activity (e.g., inhibition of platelet aggregation) might disappear [Fregnan, G. B. & Berte, F., "Enhancement of specific biological activity of dipyridamole by complexation with β-cyclodextrin," *Pharmacology* 40, 96 (1990)]. Inclusion complexes of dipyridamole with β-cyclodextrins are reported to give quicker and higher blood levels with smaller inter-individual variability [Fregnan & Berte, supra]. Therapeutic concentrations of dipyridamole have been reported to be in the range of about 2 to 6 µM [Boeynaems, J. M. et al., "Dipyridamole and vascular prostacyclin production," *Biochemical Pharmacol.* 35, 2897 ( 1986)]; adenosine-mediated inhibition is reported first to appear in undiluted human blood at about $1 \times 10^{-6}$ M dipyridamole, with full effects seen at $1 \times 10^{-5}$ M [Dawicki, D. D. et al., "Role of adenosine uptake and metabolism by blood cells in the antiplatelet actions of dipyridamole, dilazep and nitrobenzylthioinosine," *Biochemical Pharmacol.* 34, 3965 (1985)]. However, in vivo plasma levels of 10–15 μM (associated with a dose of 40 mg/kg dipyridamole) have been reported as necessary to reduce [$^3$H]thymidine incorporation into the DNA of rat bone marrow and gastrointestinal tract epithelium; dipyridamole at 10 mg/kg (corresponding to plasma levels of <5 μM) did not reduce [$^3$H]thymidine incorporation [Newell, D. R. et al., "The effect of the nucleoside transport inhibitor dipyridamole on the incorporation of [$^3$H]thymidine in the rat," *Biochemical Pharmacol.* 35, 3871 (1986)].

In the model systems employed in the examples reported herein, the exemplary compound dipyridamole was shown to reduce the incidence of peritoneal adhesions at concentrations of about 0.0125 mg/ml to about 0.6 mg/ml with continuous release throughout the postsurgical interval using an Alzet miniosmotic pump at a rate of 10 μl/hour. For purposes of preventing adhesion formation in accordance with the present invention, it is not believed that high systemic levels of active agent would be necessary; after oral and intravenous administrations, dipyridamole appears to be poorly absorbed and has a high apparent clearance [see, e.g., Bjornsson, T. D. et al., "Effective antiplatelet drug concentrations in experimental arterial thromboembolism," *Thrombosis Research* 48, 337 (1987)]. Rather, local concentrations of active agent on the order of about 0.5 μg/ml to about 60 mg/ml, and preferably about 12.5 μg/ml to about 0.6 mg/ml, would be effective in accordance with the present invention. Based upon the weight of a typical human patient, this would correspond to a range of 0.053 ng/cm$^2$/hr to 6.4 μg/cm$^2$/hr or 0.021 ng/cm$^2$/hr/kg to 2.6 μg/cm$^2$/hr/kg for dipyridamole and analogs thereof; the preferred range is 0.00133 μg/cm$^2$/hr to 0.064 μg/cm$^2$/hr or 0.53 ng/cm$^2$/hr/kg to 0.026 μg/cm$^2$/hr/kg. When the active agent is administered in the form of a copolymer, dosages would be calculated so as to provide equivalent amounts of dipyridamole or analog thereof.

The active agents in accordance with the present invention may be administered directly in a suitable vehicle, for example a solution of tartaric acid and polyethylene glycol (PEG), at a site at which it is desired to prevent adhesion formation. Pursuant to preferred embodiments of the present invention, however, at least one active agent in accordance with the present invention is administered in a single dose delivery (for example, prior to suturing after surgery) using a drug-delivery system which enables the maintenance of requisite concentrations of the compound for a period of time sufficient for re-epithelialization. A suitable drug-delivery system would itself be essentially non-inflammatory and nonimmunogenic; in addition, it would permit release of the active agent so as to maintain effective levels thereof over the desired time period. A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems, such as DepoFoam extended-release formulations comprising spherical particles bounded by a single bilayer lipid membrane and each containing numerous nonconcentric aqueous chambers which encapsulate the active ingredient [see, e.g., Kim, T. K. et al., "Extended-release formulation of morphine for subcutaneous administration," *Cancer Chemother. Pharmacol.* 33, 187 (1993); Chatelut, E. et al., "A slow-release methotrexate formulation for intrathecal chemotherapy," *Cancer Chemother. Pharmacol.* 32, 179 (1993)]; viscous instillates; absorbable and/or biodegradable mechanical barriers; and polymeric delivery materials, such as polyethylene oxide/polypropylene oxide block copolymers (e.g., poloxamers), poly-orthoesters, cross-linked polyvinyl alcohol, polyanhydrides, polymethacrylate and polymethacrylamide hydrogels, anionic carbohydrate polymers, etc. Useful delivery systems are well known in the art and are described in, e.g., U.S. Pat. No. 4,937,254 to Sheffield et al., the entire disclosure of which is hereby incorporated by reference.

One particularly suitable formulation to achieve the desired near zero-order release of an active agent in accordance with the present invention comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 μm offer advantages over other delivery systems. For example, they generally use less active agent and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation. Of course, these biodegradable polymers (such as lactide and caprolactone polymers) may alternatively be used in formulations other than microcapsules or microspheres; for example, pre-made films and spray-one films of these polymers containing the active agent would be suitable for use in accordance with the present invention.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters such as crystallinity, molecular weight and composition. In particular, adjustment in the amount of drug released is generally achieved by modification of capsule wall thickness, capsule diameter, or both. Detailed information concerning the design, preparation and use of microspheres and microcapsules is provided by, e.g., Lewis, D. H., "Controlled Release of Bioactive Agents from Lactide/Glycolide Polymers," in *Biodegradable polymers as drug delivery systems*, Jason & Langer, eds., pp. 1–41 (1990), the entire disclosure of which is hereby incorporated by reference. The sustained intraperitoneal release of an active agent (dexamethasone) using poly(lactide-coglycolide) microparticles is described in Hoeckel, M. et al., "Prevention of Peritoneal Adhesions in the Rat with Sustained Intraperitoneal Dexamethasone Delivered by a Novel Therapeutic System," *Annales Chirurgiae et Gynaecologiae*

76:306–313 (1987), the entire disclosure of which is also incorporated by reference.

As is well known to those skilled in the art, various methods are currently available for preparing microcapsules, any of which could be employed to provide formulations in accordance with the present invention. Biodegradable polymeric materials suitable for preparation of microcapsules for controlled (i.e., near zero-order) release would be readily determined through routine experimentation by those skilled in the art. Moreover, alternative delivery systems suitable for use in accordance with the present invention (for example, fibers or filaments comprising the active agents) based on biodegradable polymers are also contemplated as within the scope of the present invention.

An alternative approach for the single-dose delivery of active agent in accordance with the present invention involves the use of liposomes. The encapsulation of an active agent in multilamellar vesicles (or liposomes) is a well known technique to assist in target drug delivery and prolong drug residence. In a typical procedure, a liposome-forming powdered lipid mixture is added to the desired quantity of active agent in aqueous solution (e.g., phosphate-buffered saline) to form a suspension. After a suitable hydration period, the hydrated suspension is then autoclaved to provide the liposome-active agent preparations. A lipid mixture suitable for formation of liposomes may be prepared from L-alpha-distearoyl phosphatidylcholine and cholesterol dissolved in chloroform, to which alpha-tocopherol is added; other compositions and methods for formation of liposomes would, however, also be useful for this purpose. The intraperitoneal administration of liposomes containing ibuprofen or tolmetin is described in Rodgers, K. et al., "Inhibition of Postsurgical Adhesions by Liposomes Containing Nonsteroidal Antiinflammatory Drugs," *Int. J. Fertil.* 35:40 (1990), the entire disclosure of which is hereby incorporated by reference. Liposomally-entrapped dipyridamole has been shown to have improved bioavailability after intraperitoneal administration in Stozek, T. & Krowczynski, L., "Bioverfuegbarkeit von Dipyridamol in Form yon Liposomen," *Pharmazie* 41, 645 (1986), the entire disclosure of which is also hereby incorporated by reference.

Yet another suitable approach for single dose delivery of active agent in accordance with the present invention involves the use of so-called viscous instillates. In this technique, high-molecular-weight carriers are used in admixture with the active agents, giving rise to an extended structure which produces a solution with high viscosity. Suitable high-molecular-weight carriers include, but are not limited to, the following: dextrans and cyclodextrans; hydrogels; crosslinked viscous materials, including viscoelastics and cross-linked viscoelastics; carboxymethylcellulose; and hyaluronic acid. While some studies have suggested that the use of viscous barrier solutions per se may have an advantageous effect in reducing the incidence of adhesion formation, it is believed that any such effect is of limited scope when compared to the combination of active agent and carrier. The intraperitoneal administration of a viscous instillate comprising tolmetin is described in Abe, H. et al., "The Effect of Intraperitoneal Administration of Sodium Tolmetin-Hyaluronic Acid on the Postsurgical Cell Infiltration In Vivo," *J. Surg. Res.* 49:322 (1990), the entire disclosure of which is hereby incorporated by reference.

Pursuant to yet another approach, active agent is administered in combination with an absorbable mechanical barrier which alone reduces adhesion formation. As would be readily apparent to one working in the field, an active agent in accordance with the present invention may be covalently or noncovalently (e.g., ionically) bound to such a barrier, or it may simply be dispersed therein. A particularly suitable mechanical barrier for use in this particular embodiment of the invention comprises oxidized regenerated cellulose; one such absorbable barrier is available under the designation INTERCEED(TC7) from Johnson and Johnson Medical, Inc., New Brunswick, N.J. [INTERCEED(TC7) Adhesion Barrier Study Group, "Prevention of postsurgical adhesions by INTERCEED(TC7), an absorbable adhesion barrier: a prospective, randomized multicenter clinical study," *Fertility and Sterility* 51,933 (1989)]. The use of a mechanical barrier as a carrier to deliver heparin to traumatized surfaces is disclosed in Diamond, M. P. et al., "Synergistic effects of INTERCEED(TC7) and heparin in reducing adhesion formation in the rabbit uterine horn model," *Fertility and Sterility* 55, 389 (1991) and Diamond, M. P. et al., "Adhesion reformation: reduction by the use of Interceed(TC7) plus heparin," *J. Gynecologic Surg.* 7, 1 (1991), the entire disclosures of which are hereby incorporated by reference.

The invention may be better understood with reference to the accompanying examples, which are intended to be illustrative only and should not be viewed as in any sense limiting the scope of the invention, which is defined hereinafter in the accompanying claims.

EXAMPLES

Multiple studies to confirm the efficacy of dipyridamole in the reduction of adhesion formation after peritoneal surgery were performed. Two model systems were employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbit were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3×3-cm area of peritoneum and transversus abdominis muscle was removed on the right lateral abdominal wall. Electrocautery was used to stop excessive bleeding. The cecum was exteriorized, and digital pressure was exerted to create subserosal hemorrhages over all cecal surfaces. The cecum was then returned to its normal anatomic position. The compound to be tested was placed in an Alzet miniosmotic pump to allow continuous release of the molecule throughout the postsurgical interval. The Alzet miniosmotic pump was placed in the subcutaneous space and a delivery tube connected the pump with the site of delivery (uterine horns of the rabbit). Vehicle was placed in the pump of control rabbits. The abdominal wall and skin were closed in a standardized manner.

After 7 days, the rabbits were sacrificed and the percentage of the area of the sidewall injury that is involved in adhesions was determined. In addition, the tenacity of the adhesion formed was scored using a 0+to 3+ system as follows:

0=no adhesions

1=mild, easily disectable adhesions

2=moderate adhesions; non-disectable, does not tear organ

3=dense adhesions; non-disectable, tears the organ when removed

A reduction in the area or the tenacity of the adhesions would be considered beneficial.

In additional experiments, a rabbit uterine horn model was employed. This model has been previously shown to cause severe adhesions in rabbits after surgery [Nishimura, K. et al., "The use of ibuprofen for the prevention of postoperative adhesions in rabbits," *Am. J. Med.* 77:102–6 (1984)]. The rabbits were anesthetized (130 mg/kg ketamine and 20 mg/kg acetylpromazine im) and prepared for sterile surgery. A midline laparotomy was performed, and surgical trauma was performed on both uterine horns by abrading the serosal surface with gauze until punctate bleeding developed. Ischemia of both uterine horns was induced by removal of the collateral blood supply. After traumatization, the abdominal wall was closed in two layers. The compound to be tested was delivered as described for the peritoneal sidewall model.

With the uterine horn model, an initial score (0 to 4+) to represent the overall extent of adhesions is given. The percentage of a surface of the horn involved in adhesions to various organs are given in the tables below the overall adhesion score.

Example 1

The efficacy of dipyridamole in preventing adhesion formation was evaluated in the sidewall model. The vehicle was 2 mg/ml tartaric acid and 50 mg/ml polyethylene glycol, pH 2.7 (a vehicle used clinically for intravenous injections). This vehicle, however, was found to be very inflammatory. In addition, it was found that the high dose (6 mg/ml) reduced the integrity of the delivery tube. In the lower dose, dipyridamole was efficacious in the reduction and only a small amount of inflammation was noted; however, some of the drug precipitated at the site of injury.

| Treatment | % Adhesions | Adhesion Tenacity |
|---|---|---|
| Vehicle Control | 80 | 2+ |
| | 100 | 3+ |
| | 50 | 2+ |
| | 90 | 2+ |
| | 100 | 3+ |
| | 100 | 3+ |
| Mean: | 86.7 | |
| 6 mg/ml Dipyridamole | 100 | 3+ |
| | 60 | 2+ |
| | 100 | 3+ |
| | 80 | 3+ |
| | 20 | 1+ |
| | 100 | 2+ |
| Mean: | 76.7 | |
| 0.6 mg/ml Dipyridamole | 20 | 1+ |
| | 10 | 1+ |
| | 50 | 1+ |
| | 10 | 2+ |
| | 0 | 0+ |
| | 10 | 1+ |
| Mean: | 16.7 | |

Example 2

The procedure was repeated to determine if dipyridamole required a certain pH in the vehicle for efficacy. It was found that dipyridamole was effective in reducing adhesion formation in both pH buffers. Adhesion formation was also less pronounced with the pH 5.0 buffer alone.

| Treatment | % Adhesions | Adhesion Tenacity |
|---|---|---|
| Control | 100 | 3+ |
| | 80 | 3+ |
| | 100 | 3+ |
| | 60 | 3+ |
| Mean: | 85.0 | |
| Vehicle (pH 2.7) | 80 | 2+ |
| | 70 | 2+ |
| | 90 | 2+ |
| | 100 | 3+ |
| Mean: | 85.0 | |
| 0.6 mg/ml Dipyridamole | 30 | 1+ |
| | 30 | 2+ |
| | 20 | 1+ |
| | 100 | 2+ |
| Mean: | 45.0 | |
| Vehicle (pH 5.0) | 20 | 1+ |
| | 40 | 2+ |
| | 0 | 0+ |
| | 80 | 1+ |
| Mean: | 35.0 | |
| 0.6 mg/ml Dipyridamole | 0 | 0+ |
| | 10 | 1+ |
| | 10 | 1+ |
| | 50 | 2+ |
| Mean: | 17.5 | |

Example 3

The effects of dipyridamole in the pH 5 buffer was examined in the double uterine horn model for adhesion prevention. In this model, the use of pH 5.0 buffer alone did not reduce adhesion formation; however, dipyridamole did show some efficacy. In addition., in this model there was no precipitation of dipyridamole, either at the site of delivery or at the site of injury.

| Treatment | Overall Adhesion Score |
|---|---|
| Control | 2.5+ |
| | 3.5+ |
| | 2.5+ |
| | 3+ |
| | 3.5+ |
| Vehicle | 2+ |
| | 3+ |
| | 2.5+ |
| | 3+ |
| | 2+ |
| | 2+ |
| 0.6 mg/ml Dipyridamole | 2.5 + |
| | 2+ |
| | 1.5+ |
| | 3.5+ |
| | 2.5+ |
| | 2+ |
| 0.06 mg/ml Dipyridamole | 1+ |
| | 1.5+ |
| | 1+ |
| | 2+ |
| | 3+ |
| | 0+ |

% ORGAN INVOLVEMENT IN UTERINE HORN ADHESION

|  | Right Horn | | | | Left Horn | | | |
| --- | --- | --- | --- | --- | --- | --- | --- | --- |
| Treatment | Bowel | Bladder | Itself | Left | Bowel | Bladder | Itself | Right |
| Control | 30 | 80 | 20 | 0 | 0 | 80 | 15 | 0 |
|  | 25 | 60 | 20 | 50 | 20 | 60 | 0 | 50 |
|  | 0 | 80 | 50 | 10 | 0 | 80 | 50 | 10 |
|  | 40 | 20 | 80 | 80 | 40 | 20 | 80 | 80 |
|  | 40 | 50 | 30 | 20 | 40 | 50 | 0 | 20 |
| Mean: | 27 | 58 | 40 | 32 | 20 | 58 | 29 | 32 |
| Vehicle | 20 | 30 | 0 | 0 | 10 | 10 | 50 | 0 |
|  | 20 | 80 | 0 | 20 | 20 | 80 | 0 | 20 |
|  | 30 | 40 | 50 | 0 | 30 | 40 | 50 | 0 |
|  | 70 | 20 | 50 | 10 | 70 | 20 | 50 | 10 |
|  | 0 | 40 | 10 | 70 | 0 | 40 | 10 | 70 |
|  | 0 | 60 | 50 | 40 | 0 | 60 | 50 | 40 |
| Mean: | 23.3 | 45 | 26.7 | 23.6 | 21.6 | 41.7 | 35 | 23.3 |
| 0.6 Dipyridamole | 80 | 50 | 20 | 0 | 80 | 50 | 30 | 0 |
|  | 10 | 10 | 80 | 0 | 10 | 10 | 20 | 0 |
|  | 25 | 0 | 50 | 0 | 20 | 0 | 50 | 0 |
|  | 30 | 80 | 80 | 0 | 30 | 80 | 50 | 0 |
|  | 30 | 50 | 40 | 0 | 30 | 50 | 40 | 0 |
|  | 10 | 60 | 50 | 0 | 10 | 60 | 50 | 0 |
| Mean: | 30.8 | 41.7 | 53.3 | 0 | 30 | 41.7 | 40 | 0 |
| 0.06 Dipyridamole | 0 | 10 | 0 | 10 | 0 | 0 | 0 | 10 |
|  | 20 | 50 | 0 | 0 | 30 | 50 | 0 | 0 |
|  | 20 | 0 | 0 | 0 | 20 | 0 | 0 | 0 |
|  | 20 | 80 | 0 | 40 | 20 | 0 | 0 | 40 |
|  | 30 | 80 | 0 | 0 | 30 | 80 | 40 | 0 |
|  | 0 | 0 | 0 | 0 | 0 | 0 | 0 | 0 |
| Mean: | 15 | 36.7 | 0 | 8.3 | 16.7 | 21.7 | 6.7 | 8.3 |

Example 4

In this series of experiments, the vehicle was Hanks Balanced Salt Solution (HBSS), pH 4.8. In addition, in the uterine horn model two pumps were used in each rabbit (one to each site of injury), so that the data would be more directly comparable. In the sidewall model, there was some precipitation of dipyridamole at the site of injury; the active agent was somewhat efficacious at adhesion prevention. There was no precipitation observed in the double uterine horn model, and dipyridamole was observed to be even more effective at adhesion prevention.

| Treatment | % Adhesions | Adhesion Tenacity |
| --- | --- | --- |
| Vehicle Control | 80 | 2+ |
|  | 70 | 3+ |
|  | 90 | 3+ |
|  | 80 | 3+ |
|  | 100 | 2+ |
| Mean: | 84.0 |  |
| 0.5 mg/ml Dipyridamole | 80 | 2+ |
|  | 20 | 1+ |
|  | 30 | 1+ |
|  | 50 | 1+ |
|  | 30 | 2+ |
| Mean: | 42.0 |  |
| 0.05 mg/ml Dipyridamole | 40 | 1+ |
|  | 100 | 3+ |
|  | 70 | 2+ |
|  | 50 | 1+ |
|  | 20 | 1+ |
| Mean: | 56.0 |  |

| | % ORGAN INVOLVEMENT IN UTERINE HORN ADHESION | | | | | | | |
| --- | --- | --- | --- | --- | --- | --- | --- | --- |
|  | Right Horn | | | | Left Horn | | | |
| Treatment | Bowel | Bladder | Itself | Left | Bowel | Bladder | Itself | Right |
| Control | 60 | 60 | 60 | 100 | 40 | 100 | 100 | 0 |
|  | 60 | 30 | 100 | 50 | 60 | 30 | 50 | 50 |
|  | 100 | 80 | 50 | 0 | 100 | 80 | 50 | 0 |
|  | 100 | 0 | 50 | 30 | 100 | 10 | 50 | 30 |
|  | 50 | 60 | 70 | 30 | 50 | 60 | 70 | 30 |
| Mean: | 74 | 46 | 66 | 42 | 70 | 56 | 64 | 22 |
| 0.5 Dipyridamole | 20 | 50 | 0 | 10 | 30 | 50 | 10 | 0 |
|  | 20 | 20 | 30 | 0 | 20 | 20 | 30 | 0 |
|  | 0 | 30 | 30 | 0 | 0 | 30 | 30 | 0 |
|  | 60 | 30 | 0 | 20 | 6 | 100 | 0 | 20 |
|  | 20 | 0 | 0 | 0 | 20 | 0 | 40 | 0 |
| Mean: | 24 | 26 | 12 | 6 | 26 | 40 | 22 | 4 |
| 0.05 Dipyridamole | 30 | 0 | 0 | 0 | 30 | 0 | 0 | 0 |
|  | 100 | 0 | 0 | 0 | 100 | 0 | 100 | 0 |
|  | 10 | 70 | 30 | 0 | 10 | 0 | 0 | 0 |
|  | 30 | 0 | 0 | 40 | 30 | 0 | 0 | 40 |

| % ORGAN INVOLVEMENT IN UTERINE HORN ADHESION | | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 20 | 0 | 50 | 0 | 20 | 0 | 50 | 0 |
| Mean: | 38 | 15 | 16 | 8 | 38 | 0 | 30 | 8 |

Example 5

In this experiment, the concentration of dipyridamole was further reduced in an attempt to eliminate precipitation of the material in the sidewall model and to determine the degree of efficacy of dipyridamole at lower concentrations in the double uterine horn model. Efficacy was observed in both models, even at the lower concentration.

| Treatment | % Adhesions | Adhesion Tenacity |
|---|---|---|
| Vehicle Control | 100 | 3+ |
| | 60 | 2+ |
| | 70 | 2+ |
| | 70 | 3+ |
| | 100 | 3+ |
| | 80 | 2+ |
| Mean: | 80.0 | |
| 0.05 mg/ml Dipyridamole | 0 | 0+ |
| | 10 | 1+ |
| | 80 | 2+ |
| | 80 | 1+ |
| | 0 | 0+ |
| | 60 | 1+ |
| Mean: | 38.3 | |
| 0.0125 mg/ml Dipyridamole | 30 | 1+ |
| | 100 | 1+ |
| | 20 | 2+ |
| | 60 | 1+ |
| | 25 | 1+ |
| | 80 | 1+ |
| Mean: | 52.5 | |

| Double Uterine Horn Model | |
|---|---|
| Treatment | Overall Adhesion Score |
| Vehicle Control | 2.5+ |
| | 3.5+ |
| | 3+ |
| | 3+ |
| | 3+ |
| | 3+ |
| 0.05 mg/ml Dipyridamole | 2+ |
| | 1+ |
| | 2+ |
| | 1.5+ |
| | 1.5+ |
| | 2+ |
| 0.0125 mg/ml Dipyridamole | 1+ |
| | 1.5+ |
| | 3+ |
| | 2+ |
| | 2+ |
| | 1.5+ |

| % ORGAN INVOLVEMENT IN UTERINE HORN ADHESION | | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 10 | 50 | 40 | 40 | 10 | 50 | 40 |
| | 30 | 60 | 40 | 80 | 30 | 60 | 40 | 80 |
| | 10 | 50 | 50 | 30 | 10 | 50 | 40 | 30 |
| | 30 | 0 | 100 | 50 | 30 | 100 | 50 | 80 |
| | 80 | 50 | 50 | 40 | 80 | 50 | 30 | 40 |
| | 50 | 60 | 50 | 50 | 50 | 60 | 50 | 50 |
| Mean: | 40 | 38.3 | 56.7 | 48.3 | 40 | 38.3 | 51.7 | 48.3 |
| 0.05 Dipyridamole | 10 | 10 | 0 | 10 | 10 | 10 | 0 | 10 |
| | 40 | 0 | 50 | 10 | 40 | 0 | 0 | 10 |
| | 30 | 0 | 30 | 0 | 30 | 0 | 40 | 0 |
| | 40 | 0 | 0 | 0 | 40 | 0 | 30 | 0 |
| | 20 | 0 | 40 | 0 | 20 | 0 | 40 | 0 |
| | 60 | 0 | 0 | 0 | 80 | 0 | 0 | 0 |
| Mean: | 33.3 | 1.7 | 20 | 3.3 | 36.7 | 1.7 | 18.3 | 3.3 |
| 0.0125 Dipyridamole | 30 | 0 | 0 | 0 | 30 | 0 | 0 | 0 |
| | 30 | 0 | 60 | 0 | 30 | 0 | 0 | 0 |
| | 20 | 40 | 50 | 30 | 20 | 50 | 30 | 30 |
| | 10 | 0 | 20 | 10 | 40 | 0 | 0 | 0 |
| | 80 | 0 | 0 | 0 | 80 | 0 | 20 | 0 |
| | 50 | 0 | 0 | 0 | 30 | 0 | 30 | 0 |
| Mean | 36.7 | 6.7 | 21.7 | 6.7 | 38.3 | 8.3 | 13.3 | 5 |

Although some efficacy was observed in the sidewall model, the lower dose of the drug apparently did not entirely overcome the inflammatory effects of the vehicle. In the double uterine horn model, both doses of dipyridamole had an effect. In this experiment, neither dose of dipyridamole affected adhesions between the uterine horn and the bowel; however, there were no adhesions in many rabbits at the site where the drug was administered (the tube was placed so the drug is administered between the bladder and the uterine horn).

Example 6

The efficacy of dipyridamole in the double uterine horn model was further evaluated in a kinetics study. In this study, the pump was disconnected at various times after surgery to determine the time period of exposure to the drug effective to reduce adhesion formation. The efficacy of dipyridamole in preventing adhesion formation was most pronounced in this study. It is suspected that longterm administration of the vehicle may be inflammatory, thereby reducing some of the early benefits of drug exposure. No inflammation was observed at the end of the tube in these rabbits, although a few rabbits exhibited petechial hemorrhage or mechanical damage from tube placement.

| Treatment | Overall Adhesion Score |
|---|---|
| Vehicle | 3+ |
| | 3.5+ |
| | 2.5+ |
| | 4+ |
| | 3.5+ |
| | 3.5+ |
| 0.15 mg/ml Dipyridamole/24 hr | 1+ |
| | 1.5+ |
| | 1.5+ |
| | 1+ |
| | 1.5+ |
| 0.15 mg/ml Dipyridamole/48 hr | 1.5+ |
| | 1+ |
| | 2+ |
| | 0.5+ |
| | 1+ |
| | 1.5+ |
| 0.15 mg/ml Dipyridamole/72 hr | 1.5+ |
| | 2+ |
| | 0.5+ |
| | 1.5+ |
| | 2+ |
| 0.05 mg/ml Dipyridamole/24 hr | 2+ |
| | 1.5+ |
| | 0.5+ |
| | 1+ |
| | 2+ |
| | 2+ |
| 0.05 mg/ml Dipyridamole/48 hr | 1.5+ |
| | 2.5+ |
| | 1+ |
| | 1+ |
| | 0.5+ |
| | 2.5+ |
| 0.05 mg/ml Dipyridamole/72 hr | 1+ |
| | 1.5+ |
| | 2+ |
| | 0.5+ |
| | 1.5+ |
| | 0.5+ |

| | % ORGAN INVOLVEMENT IN UTERINE HORN ADHESION | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 80 | 10 | 70 | 0 | 80 | 10 | 100 | 0* |
| | 40 | 50 | 70 | 60 | 40 | 50 | 70 | 60 |
| | 30 | 0 | 80 | 80 | 70 | 0 | 80 | 80 |
| | 100 | 80 | 60 | 50 | 100 | 800 | 60 | 50 |
| | 30 | 100 | 40 | 50 | 50 | 100 | 40 | 50* |
| | 80 | 60 | 80 | 80 | 80 | 60 | 80 | 80 |
| Mean: | 60 | 50 | 66.7 | 53.3 | 70 | 50 | 71.7 | 53.3 |
| 0.15 | 0 | 10 | 10 | 0 | 0 | 10 | 10 | 0 |
| Dipyridamole/ | 10 | 0 | 0 | 10 | 10 | 0 | 0 | 10 |
| 24 hr. | 10 | 10 | 0 | 10 | 10 | 10 | 0 | 10 |
| | 30 | 0 | 0 | 0 | 30 | 0 | 0 | 0 |
| | 0 | 10 | 20 | 30 | 0 | 10 | 0 | 30 |
| Mean: | 10 | 6 | 6 | 10 | 10 | 6 | 2 | 10 |
| 0.15 | 0 | 20 | 50 | 0 | 0 | 20 | 30 | 0 |
| Dipyridamole/ | 10 | 0 | 10 | 0 | 0 | 0 | 0 | 0* |
| 48 hr. | 30 | 0 | 60 | 0 | 30 | 0 | 0 | 0 |
| | 0 | 10 | 0 | 10 | 0 | 10 | 0 | 10 |
| | 0 | 40 | 20 | 0 | 0 | 40 | 0 | 0 |
| | 10 | 10 | 0 | 20 | 10 | 10 | 0 | 20 |
| Mean: | 8.3 | 13.3 | 23.3 | 5 | 6.7 | 13.3 | 5 | 5 |
| 0.15 | 0 | 0 | 0 | 10 | 0 | 20 | 0 | 10* |
| Dipyridamole/ | 0 | 0 | 30 | 30 | 0 | 0 | 30 | 30* |
| 72 hr. | 0 | 10 | 60 | 0 | 0 | 10 | 60 | 0 |
| | 0 | 20 | 30 | 0 | 0 | 30 | 30 | 0 |
| | 30 | 30 | 30 | 0 | 0 | 30 | 30 | 0 |
| Mean: | 6 | 12 | 26 | 8 | 0 | 16 | 24 | 8 |
| 0.05 | 20 | 30 | 0 | 0 | 20 | 20 | 20 | 0 |
| Dipyridamole/ | 30 | 0 | 0 | 40 | 30 | 0 | 0 | 40 |
| 24 hr. | 0 | 10 | 30 | 0 | 0 | 10 | 30 | 0 |
| | 0 | 10 | 0 | 0 | 0 | 10 | 20 | 0 |
| | 0 | 40 | 50 | 0 | 0 | 40 | 20 | 0 |
| | 20 | 10 | 60 | 0 | 20 | 10 | 60 | 0 |
| Mean: | 11.7 | 16.7 | 23.3 | 6.7 | 11.7 | 15 | 25 | 6.7 |
| 0.05 | 10 | 10 | 10 | 0 | 10 | 10 | 0 | 0 |
| Dipyridamole/ | 0 | 40 | 20 | 20 | 0 | 40 | 20 | 20 |
| 48 hr. | 10 | 10 | 0 | 10 | 10 | 10 | 0 | 10 |
| | 0 | 0 | 50 | 10 | 0 | 0 | 0 | 10 |
| | 0 | 10 | 20 | 0 | 0 | 0 | 0 | 0 |

-continued

| | % ORGAN INVOLVEMENT IN UTERINE HORN ADHESION | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 30 | 20 | 20 | 0 | 30 | 20 | 50 | 0 |
| Mean: | 8.3 | 15 | 20 | 6.7 | 8.3 | 13.3 | 11.7 | 8.3 |
| 0.05 | 0 | 20 | 0 | 10 | 0 | 20 | 0 | 10 |
| Dipyridamole/ | 0 | 0 | 0 | 40 | 0 | 0 | 20 | 40 |
| 72 hr. | 0 | 0 | 0 | 10 | 10 | 0 | 0 | 40 |
| | 10 | 0 | 10 | 0 | 5 | 0 | 0 | 0 |
| | 0 | 20 | 20 | 0 | 0 | 20 | 20 | 0 |
| | 0 | 20 | 0 | 0 | 0 | 0 | 20 | 0 |
| Mean: | 17 | 10 | 5 | 10 | 2.5 | 6.7 | 10 | 15 |

In summary, dipyridamole has been shown to be effective in preventing the formation of adhesions in two animal models. Even if the drug is delivered by Alzet pump only for the first 24 hours after surgery, dipyridamole was effective in reducing the formation of adhesions in a rabbit double uterine horn model.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for prevention in mammals of formation of adhesions between organ surfaces at a location in need thereof, comprising:
   administering an effective amount of at least one compound selected from the group consisting of dipyridamole, RA 233, R-E 244 and RX-RA85 as active agent to provide an effective local concentration at the location for a period of time sufficient to permit tissue repair.

2. A method according to claim 1, wherein the location in need has had trauma and the period of time is about 24 hours to about 7 days after said trauma.

3. A method according to claim 1, wherein the active agent is administered in conjunction with a delivery vehicle which facilitates maintaining the effective local concentration of active agent.

4. A method according to claim 1, wherein the effective local concentration is between about 0.5 µg/ml and about 60 mg/ml.

5. A method according to claim 4, wherein said effective local concentration is between about 12.5 µg/ml and about 0.6 mg/ml.

6. A method according to claim 1, wherein the active agent is administered in the form of microcapsules or microspheres.

7. A method according to claim 6, wherein the microcapsules or microspheres comprise a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyorthoesters, polyacetals and mixtures thereof.

8. A method according to claim 1, wherein the active agent is administered in the form of a lipid-based delivery system.

9. A method according to claim 8, wherein the lipid-based delivery system is selected from the group consisting of liposomes comprising L-alpha-distearoyl phosphatidylcholine and extended-release formulations comprising spherical particles bounded by a single bilayer lipid membrane and each containing a plurality of nonconcentric aqueous chambers which encapsulate the active ingredient.

10. A method according to claim 1, wherein the active agent is administered as an intraperitoneal infusion.

11. A method according to claim 10, wherein the intraperitoneal infusion is administered by a miniosmotic pump.

12. A method according to claim 1, wherein the active agent is administered in the form of an instillate.

13. A method according to claim 12, wherein the instillate comprises a high-molecular-weight carrier selected from the group consisting of dextrans, cyclodextrans, hydrogels, carboxymethylcellulose, hyaluronic acid, chondroitin sulfate and mixtures thereof.

14. A method according to claim 1, wherein the active agent is administered in combination with an absorbable mechanical barrier.

15. A method according to claim 14, wherein the absorbable mechanical barrier comprises oxidized regenerated cellulose.

\* \* \* \* \*